United States Patent [19]

Haswell

[11] Patent Number: 5,520,041
[45] Date of Patent: May 28, 1996

[54] HUMIDITY-INDICATING MEDICAL SAMPLE SYSTEM AND METHOD

[75] Inventor: James S. Haswell, Olathe, Kans.

[73] Assignee: Beckwell International, Inc., Olathe, Kans.

[21] Appl. No.: 229,022

[22] Filed: Apr. 18, 1994

[51] Int. Cl.⁶ .............. G01N 31/22; G01J 1/48; G01W 1/00
[52] U.S. Cl. .............. 73/29.04; 73/31.03; 73/73; 436/808; 435/805; 422/55; 422/57; 422/61; 422/86
[58] Field of Search .............. 73/29.04, 24.04, 73/31.01, 73; 436/808; 435/805; 422/55, 56, 57, 58, 61, 86

[56] References Cited

U.S. PATENT DOCUMENTS

| | | | |
|---|---|---|---|
| 2,214,354 | 9/1940 | Snelling | 116/114 |
| 2,249,867 | 7/1941 | Snelling | 73/335 |
| 2,250,980 | 7/1941 | Workman et al. | 229/55 |
| 3,386,807 | 6/1968 | Edenbaum | 23/253 |
| 3,748,272 | 7/1973 | Wenz et al. | 252/194 |
| 3,881,873 | 5/1975 | Klowder | 23/253 TP |
| 4,305,720 | 12/1981 | Bernstein | 23/230 B |
| 4,748,114 | 5/1988 | Kallies et al. | 435/14 |
| 4,771,631 | 9/1988 | Lehtikoski et al. | 73/73 |
| 4,871,077 | 10/1989 | Ogden et al. | 215/366 |
| 4,902,478 | 2/1990 | Hambleton | 422/56 |
| 4,959,196 | 9/1990 | Moisson | 422/82.05 |
| 5,035,860 | 7/1991 | Kleingeld et al. | 422/61 |
| 5,084,041 | 1/1992 | Oxley et al. | 604/410 |
| 5,112,768 | 5/1992 | Carver | 436/39 |
| 5,183,742 | 2/1993 | Omoto et al. | 435/14 |
| 5,186,900 | 2/1993 | Jensen et al. | 422/104 |
| 5,192,500 | 3/1993 | Treddenick | 422/56 |
| 5,194,224 | 3/1993 | Plötz et al. | 422/55 |
| 5,224,373 | 7/1993 | Williams et al. | 73/29.02 |
| 5,364,593 | 11/1994 | Mihaylov et al. | 422/87 |
| 5,372,429 | 12/1994 | Beaver, Jr. et al. | 383/109 |
| 5,415,838 | 5/1995 | Rieger et al. | 422/57 |
| 5,439,648 | 8/1995 | Balderson et al. | 422/86 |

*Primary Examiner*—Hezron E. Williams
*Assistant Examiner*—J. David Wiggins
*Attorney, Agent, or Firm*—Litman, McMahon and Brown

[57] ABSTRACT

A medical specimen collection system includes a blood specimen collection subsystem including a blood specimen card. The blood specimen card comprises a blotter-type absorbent material with locations for receiving blood droplets. A humidity-indicating pouch comprising, for example, a cobalt chloride composition applied to blotter-type absorbent substrate is mounted on the blood specimen card in fluidic communication therewith. The humidity-indicating patch changes color in response to changing moisture levels. The blood specimen card must have less than a predetermined moisture content for processing of the samples thereon. The system can comprise a prepackaged kit which also includes a urine specimen collection subsystem and a labeling/mailing subsystem with adhesive labels and a mailing envelope. A medical specimen collection method includes the steps of obtaining blood and urine specimens, indicating a moisture content of a blood specimen card, drying the blood specimen card if necessary and mailing the collective specimens.

22 Claims, 3 Drawing Sheets

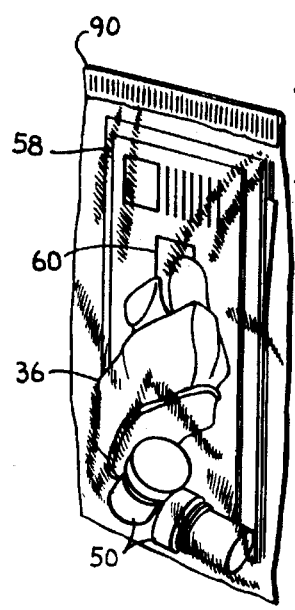
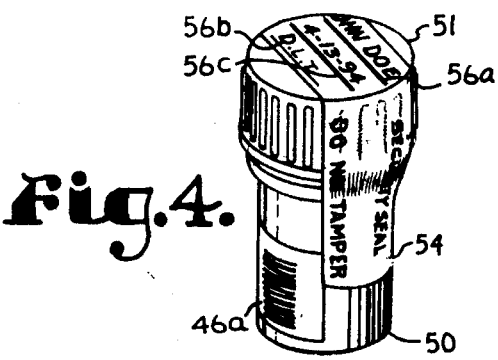
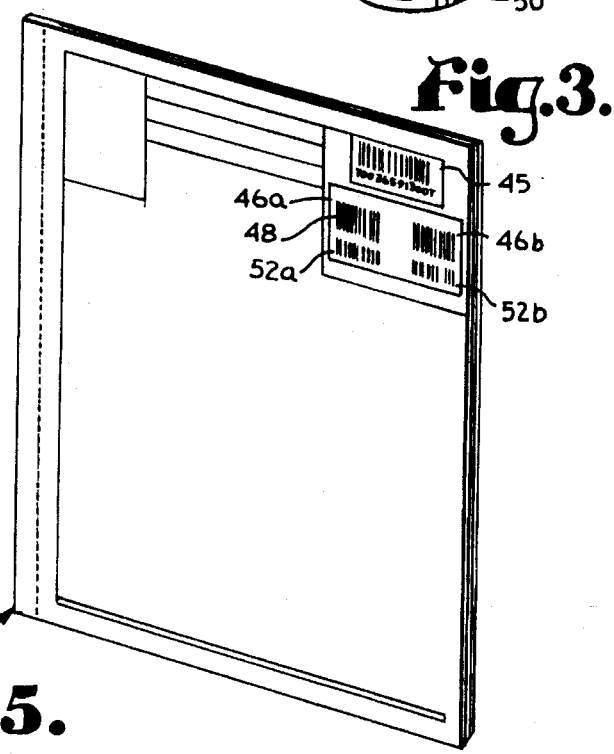
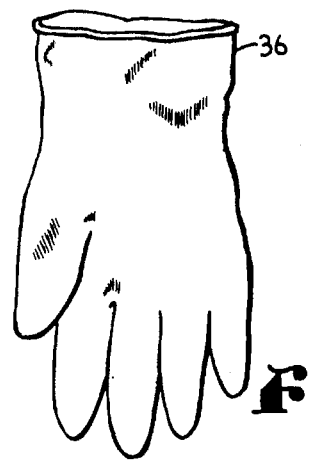
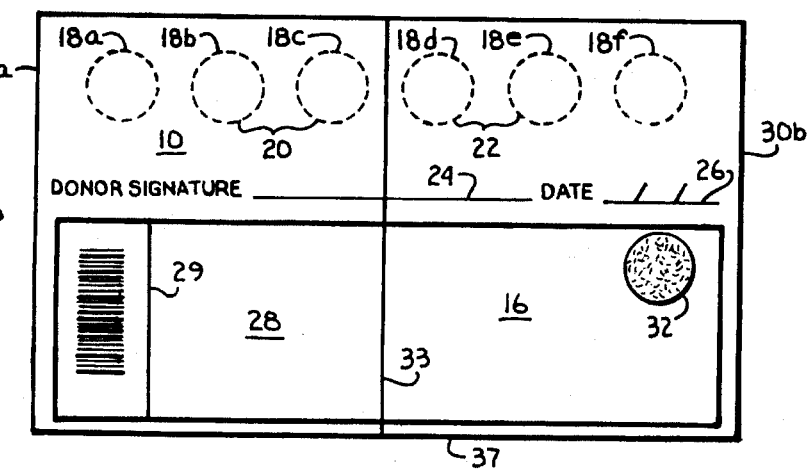

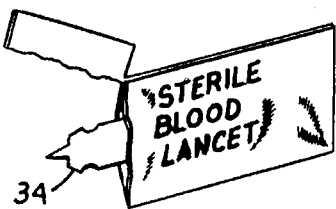
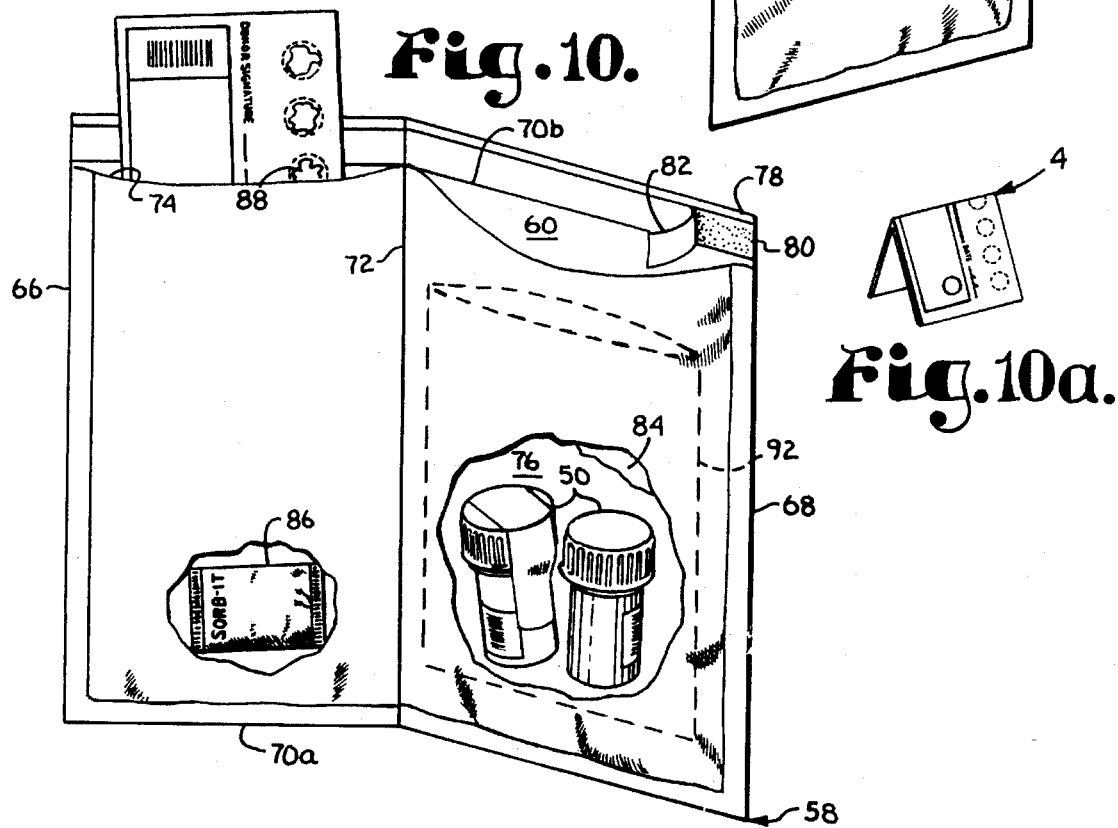

HUMIDITY-INDICATING MEDICAL SAMPLE SYSTEM AND METHOD

BACKGROUND OF THE INVENTION

1. Field of the Invention

The present invention relates generally to medical sampling, and in particular to a system for collecting blood and urine specimens including a blood specimen collection card with a humidity-indicating patch.

2. Description of the Related Art

Medical samples are used in a variety of applications to determine various characteristics of a subject, such as the presence of various diseases and/or the use of illicit drugs. Blood and urine samples from the subject are commonly obtained and analyzed to obtain such information about the subject.

Insurance companies and employers have become particularly active in testing potential insureds and employees respectively for the H.I.V. virus and/or evidence of illicit drug use. Accordingly, large numbers of insurance and job applicants are routinely referred to testing centers for the purpose of providing specimens. In many cases the analysis of the collected specimens is done at centralized laboratories or testing facilities. An examiner therefore obtains the necessary samples and transports them to the laboratory, along with information concerning the subject, the test procedure, etc.

Increased scrutiny on the part of both employers and insurers of their prospective employees and insureds has led to more widespread medical testing involving subjects' body fluids. Since significant decisions (e.g., extending employment or insurance) are often based on such test results, there is a great need for accuracy and reliability in connection with such tests. Moreover, the collected specimens must be guarded against tampering or adulteration. Still further, specimens such as blood must be dry in order to be processed and tested. Blood samples have heretofore been collected on cards, which can comprise porous, blotter-like material. However, if the cards have too high a moisture content, the specimens or samples will not dry properly. Moreover, a variety of environmental conditions can contribute to excessive moisture levels and prevent proper drying of the sample or specimens.

Accordingly, it is desirable to monitor the humidity level or moisture content of a blood specimen card from a time prior to use to a time when the dried blood samples are removed therefrom for analysis.

Various humidity-indicating devices have previously been employed to meet the requirements of particular applications. For example, low cost humidity indicators are often manufactured from absorbent materials such as blotter paper impregnated with chemical substances for indicating moisture levels. For example, the Snelling U.S. Pat. No. 2,214,354 discloses a dampness detecting and indicating device which employs water-soluble dyes in deliquescent materials which absorb moisture and thereby become liquid, mixing with and activating the dye material.

The Williams et al. U.S. Pat. No. 5,224,373 discloses a flexible humidity indicator and container which employs a chemical solution of cobalt chloride and additives on a vapor permeable layer of flash spun, film fibril high density polyethylene material.

Since blood sample cards are typically destroyed after use a moisture indicating system should be relatively inexpensive, but capable of producing results which are sufficiently accurate to facilitate proper testing procedures. Moreover, it is desirable to provide a system, e.g., in prepackaged kit form, for collecting both blood and urine specimens in one examination and mailing such specimens in a single, compartmentalized envelope.

Heretofore there has not been available a medical specimen collection system with a humidity-indicating blood sample card or a collection method with the advantages and features of the present invention.

SUMMARY OF THE INVENTION

In the practice of the present invention, a medical specimen collection system is provided which includes a blood specimen collection subsystem having a blood specimen card. The blood specimen card comprises an absorbent material such as blotter paper. A humidity-indicating patch, e.g., blotter paper impregnated with cobalt chloride and other additives, is mounted on the card in fluidic communication therewith for indicating by color change if the card moisture content is above or below a predetermined level or range. The medical specimen collection system also includes a urine specimen collection subsystem having a pair of urine collection vials and a labeling/mailing subsystem including bar code labels for the blood specimens card and the urine collection vials, and a foil-lined envelope with separate pockets for the blood specimen card and the urine vials. A desiccant packet is placed in the envelope pocket along with the blood specimen card for absorbing moisture therefrom with the envelope and the collected specimens in transit. A medical specimen collection method is disclosed which includes the steps of indicating a moisture content of the blood specimen card, drying the card if necessary, collecting blood samples thereon, drying the blood samples, collecting a urine specimen, labeling the specimens and mailing the specimens.

OBJECTS AND ADVANTAGES OF THE INVENTION

The principal objects and advantages of the present invention include providing a medical specimen collection system; providing such a system which includes a blood sample card; providing such a system which includes a humidity-indicating patch on the blood specimen card; providing such a system wherein the humidity-indicating patch changes color in response to varying moisture levels of the card; providing such a system with disposable components; providing such a system adapted for collection of blood and urine specimens; providing such a system including an envelope for mailing a blood sample card and urine specimen vials in separate, lined compartments; and providing a medical specimen collection system and method, including a humidity-indicating blood sample card, which are efficient in operation, economical to manufacture and particularly well adapted for the proposed usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an upper left side perspective view of a humidity-indicating medical sample system embodying the present invention and shown in a prepackaged form.

FIG. 2 is a front elevational view of a blood sample card thereof.

FIG. 3 is an upper, front, left side perspective view of a test information form thereof.

FIG. 4 is an upper perspective view of a urine vial thereof.

FIG. 5 is an upper perspective view of a latex glove thereof.

FIG. 6 is an upper perspective view of an alcohol-soaked pad thereof.

FIG. 7 is a perspective view of a lancet thereof.

FIG. 8 is a perspective view of an adhesive bandage thereof.

FIG. 9 is a perspective view of a gauze pad thereof.

FIG. 10 is a perspective view of a mailing envelope thereof.

FIG. 10a is an upper perspective view of a blood specimen card thereof shown in a "tented" drying configuration thereof.

DETAILED DESCRIPTION OF THE PREFERRED EMBODIMENTS

I. Introduction and Environment

Figure 11:
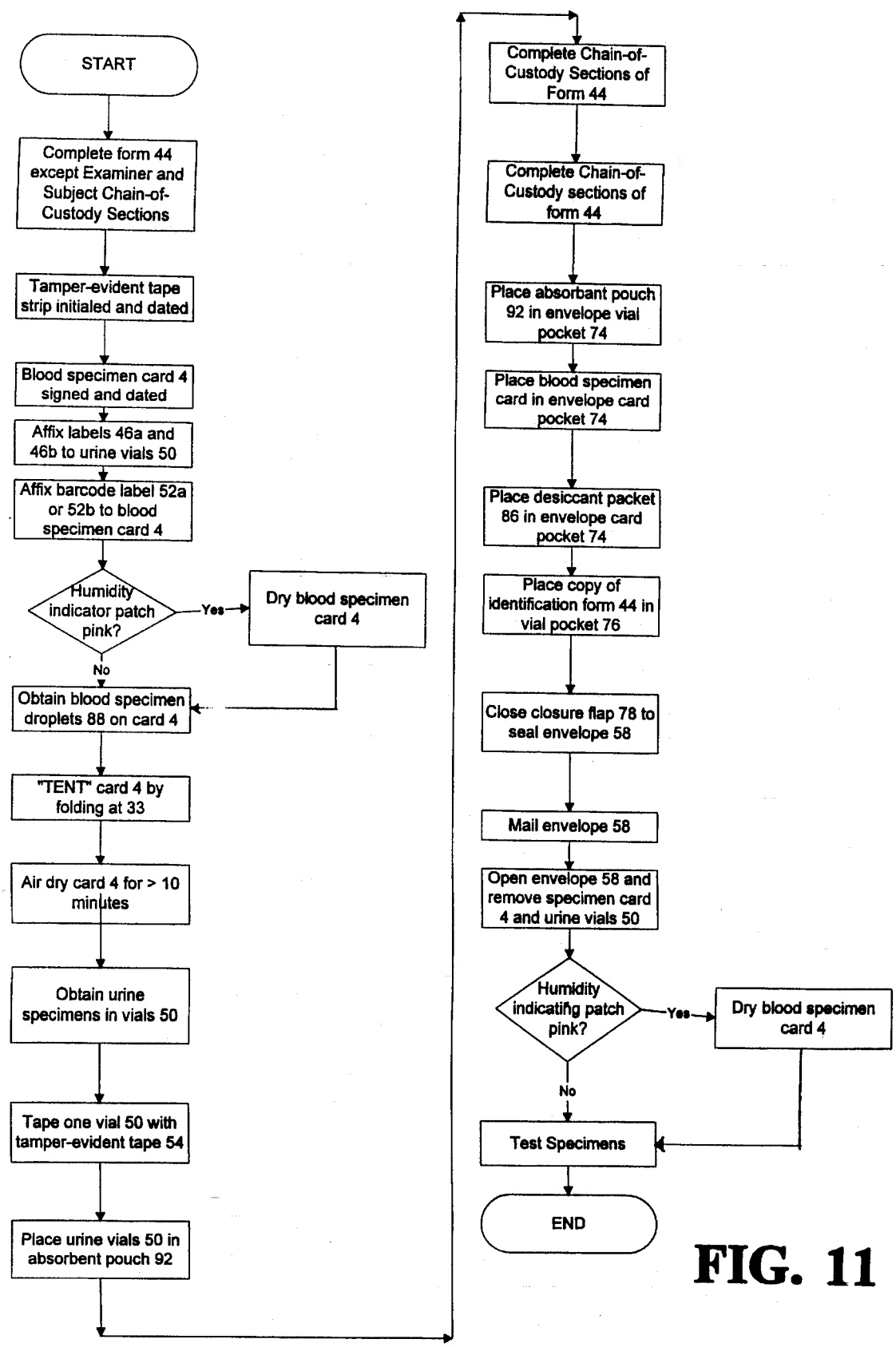
FIG. 11 is a flowchart showing the steps of a humidity-indicating medical sample method embodying the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Certain terminology will be used in the following description for convenience in reference only and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the embodiment being described and designated parts thereof. Said terminology will include the words specifically mentioned, derivatives thereof and words of a similar import.

Referring to the drawings in more detail, the reference numeral 2 generally designates a medical specimen collection system embodying the present invention. The system 2 generally comprises a blood specimen collection subsystem 3 including a humidity-indicating blood collection card 4, a urine specimen collection subsystem 6 and a labeling/mailing subsystem 8.

II. Blood Specimen Collection Subsystem 3

The blood specimen card 4 includes a front or printed face 10 and a back or plain face 12. The front face 10 includes upper and lower portions 14, 16. The upper portion 14 includes a plurality (e.g., six are shown) of specimen locations 18a–18f. The specimen locations 18a–18f are defined by dashed lines 20 forming circles 22 on the card printed face upper portion 14. The upper portion 14 also includes signature and date lines 24, 26 printed thereon.

The card printed face lower portion 16 includes a test result area 28 which can be reserved for use by testing laboratory personnel for noting test results. Adjacent to the test result area 28, e.g. adjacent to a card side edge 30a, an identification label area can be provided. Adjacent to the other card side 30b a humidity-indicating patch 32 is adhesively mounted on the card front face 10, e.g., in the upper right-hand corner of the test result area 28. The humidity indicating patch is fluidically connected to the substrate blood specimen card 4. Both the blood specimen card 4 and the humidity-indicating patch 32 can comprise, for example, cotton fibers. Other types of blotting paper, e.g., a flash spun, film fibril sheet of high density polyethylene, such as Tyvek material from E. I. DuPont de Nemours & Co. The humidity-indicating patch 32 can comprise a 65% relative humidity indicator patch, which is available from the Humidial Corporation, P.O. Box 610, 465 N. Mt. Vernon Ave., Colton, Calif., 92324-0610.

The humidity-indicating patch 32 can comprise blotting paper with cobalt chloride indicating materials applied thereto, and additional chemical additives if desired. Preferably the humidity indicating patch 32 displays a blue color when the moisture content of the card 4 is below a predetermined level, and displays a pink or violet color when the moisture content of the card 4 is above such a predetermined level. Preferably the humidity indicating patch 32 is reversibly alterable in color, i.e., changing from blue to pink to response to a moisture content greater than the predetermined limit, and changing from pink to blue as the card dries. A fold line 33 extends between upper and lower margins 35, 37 of the card 4.

In addition to the blood specimen card 4, the blood specimen collection subsystem 3 includes a lancet 34 for piercing a subject's fingers and a pair of latex gloves 36 to be worn by the person responsible for obtaining, labeling and mailing the samples and other pertinent information. A sterilizing pad 38 with a suitable disinfectant, e.g., alcohol, etc., is provided for cleaning the puncture area in advance.

A sterile gauze pad 40 and an adhesive bandage 42 are provided for stopping the blood flow and covering the puncture site respectively.

III. Urine Specimen Collection Subsystem 6

The urine specimen collection subsystem 6 includes a pair of urine specimen vials 50, which can be equipped with screw-type lids 51. A tamper-evident tape strip 54 is provided for placement over the cap of a urine collection vial 50. The tamper-evident tape strip 54 includes lines for the subject's name, the examiner's initials and the date of the examination 56a, 56b, 56c.

IV. Labeling/Mailing Subsystem 8

A multi-part (e.g., four parts are shown) identification form 44 includes information concerning the subject, the test and the collection of the samples. Blood sample card bar code labels 46a, 46b are adhesively mounted on the identification form 44. Urine vial Bar code labels 52a, 52b are provided for application to the urine collection vials 50. The labels 46a, 46b and 52a, 52b and the form 44 include matched bar code indicia 48 printed thereon.

An envelope 58 can be provided which includes a front panel 60 with preprinted indicia 62 thereon, such as a return address, postage, etc. The envelope 58 also includes a back panel 64 to which the front panel 60 is connected along the envelope top 66, bottom 68, one side 70a and along a medial connection strip 72. The medial connection strip 72 divides the envelope 58 into an upper/card pocket 74 and a lower/vial pocket 76. A closure flap 78 is provided along the other envelope side 70b as an extension of the front panel 60 and includes an adhesive strip 80 which is exposed when a cover strip 82 is removed whereby the closure flap 78 can be folded over the side 70b for adhesive attachment to the back panel 64.

The envelope 58 is preferably lined with a fluid-impervious material, such as foil 84, to avoid saturation of the envelope exterior in the event of a leak or spill, e.g., from the urine vials 50. The foil liner 84 serves another purpose, i.e., enclosing the blood specimen card 4 within a substantially fluid-tight upper/card pocket 74. A packet of desiccant 86 is provided for placement in the upper/card pocket 74 to absorb moisture therein and to facilitate drying of the blood specimen card 4 and the blood droplets 88 thereon. The liner 84 thus prevents moisture from outside the envelope 58 from entering the upper/card pocket 74 and retains the moisture therein for absorption by the desiccant packet 86.

V. Operation

The medical collection system 2 can be prepackaged in an individual package 90 for use with an individual subject. In addition to the kit components mentioned above, the package 90 can include informational literature about health topics, instructions for use of the system 2, etc.

The system 2 and the card 4 of the present invention can be used in connection with various procedures. The following is an example of a procedure for obtaining specimens from an individual subject. (Insert: a fluid-absorbent pouch 92 is provided for receiving the urine vials 50 and can comprise a multi-layered material, including impervious and absorbent layers, of the type which is available from Beckwell International, Inc. (the Assignee of the present application) under its trademark "Uri-Sorb". The pouch 92 is preferably sized to fit in the lower/vial pocket 76.)

A. Prepare the identification form in the tamper-evident tape strip 54.

1. The identification form 44 is completed except for examiner chain-of-custody and subject chain-of-custody sections.

2. The tamper-evident tape strip 54 is initialled and dated by the examiner and signed by the subject.

3. The blood specimen card 4 is signed and dated by the subject. The bar code labels 46a,b and 52a are applied to the vial 50 and to the card test result area 28. (Insert: the test result area 28 includes a bar code label area 29 in proximity to the card side 30a. The identification form 44 includes a preprinted bar code-label 45 which matches the bar codes on the labels 46a,b and 52a,b which labels can be adhesively attached to the identification form 44 for removal therefrom and application to the card 4 and the vials 50.)

B. Collection of blood and urine specimens.

1. Check the humidity-indicator patch 32. If blue, proceed. If pink, fold the card 4 along the fold line 33 to form a tent configuration and allow it to dry until the humidity indicator patch 32 turns blue. The card 4 should not be used if the humidity-indicator patch 32 is pink.

2. The subject should wash his or her hands in warm water, and shake a hand vigorously for about 15 seconds to provide good blood flow.

3. The subject's finger (preferably the middle or ring finger) should be cleaned with the alcohol pad 38 and dried with the gauze pad 40.

4. The examiner should put on the gloves 36. The sterile lancet 34 is used to puncture the finger (preferably avoiding the side and tip). The lancet 34 should be disposed-of pursuant to an OSHA-approved method for medical waste disposal.

5. The first drop of blood should be wiped on the gauze pad 40, whereafter each of the specimen locations 18a–f should receive a blood droplet to preferably fill and saturate the circles 22. The subject's arm should be held downwardly with the hand below heart level. Gentle pressure can be applied to the finger to stimulate blood flow if necessary. Preferably only the blood droplet should contact the card 4. The specimen locations 18a–f should be saturated one-at-a-time, and blood should not be reapplied to a circle 22 which has already received a blood droplet.

6. The gauze pad 40 can be used to stop or control the bleeding, and then disposed of pursuant to an OSHA-approved method of disposing of medical waste. The adhesive bandage 42 can then be applied to the puncture.

7. The blood specimen card 4 should then be folded along the fold line 33 and placed in a "tent" configuration (FIG. 10a to facilitate air drying of the blood specimen droplets 88.

8. The subject urinates into a urine collection cup.

9. The examiner pours the urine from the urine collection cup into the two urine collection vials 50, which are then capped securely. The signed and dated tamper-evident tape strip 54 is placed over the top of one of the urine vials, avoiding the bar code label 46a or 46b. The urine collection cup is disposed of by OSHA-approved methods for disposal of medical waste.

10. The examiner disposes of the gloves 36 by OSHA-approved methods for disposal of medical waste.

C. After specimen collection.

1. The chain-of-custody sections on the identification form 44 are completed by the examiner and the subject.

2. The four copies of the identification form can be distributed one each to the laboratory in the pouch 92 with the urine collection vials 50, to the client or customer (e.g., potential employer or insurer requesting the examination; to the examiner and to the subject).

D. Packaging and shipping

1. The urine vials 50 are placed in the fluid-absorbent pouch 92.

2. The pouch 92 is placed in the envelope lower pocket 76.

3. One of the identification form 44 copies is placed in the lower envelope pocket 76.

4. The dried (blue humidity-indicator patch 32) blood specimen card 4 is placed in the envelope upper pocket 74.

5. The desiccant packet 86 is placed in the envelope upper pocket 74 along with the blood specimen card 4 preferably against the card 4 back face 12. The blood specimen card 4 should not be placed in the lower envelope pocket with the identification form 44 or the urine collection vials 50.

6. The cover strip 82 is removed from the closure flap 78 to expose the adhesive strip 80, the closure flap 78 is folded over the envelope side edge 70 and secured to the envelope back panel 64.

7. The envelope 58 is mailed to the appropriate laboratory designated on a pre-printed address label for future analysis.

E. Receipt and processing

1. Upon receipt, the humidity-indicator patch 32 is examined. If blue, the specimen droplets 88 should be sufficiently dry for testing. If pink, the card 4 needs to be dried until the humidity-indicator patch 32 turns blue before proceeding. The blood droplet samples 88 can be scraped off of the card 4 for testing.

2. During transit, the moisture level of the card 4 will tend to normalize, with moisture being absorbed therefrom and from the atmosphere trapped within the envelope upper pocket 74 by the desiccant packet 86.

It is to be understood that while certain forms of the present invention have been illustrated and described herein, it is not to be limited to the specific forms or arrangement of parts described and shown.

What is claimed and desired to be secured by Letters Patent is as follows:

1. A humidity-indicating medical sample card which includes:
   (a) medical specimen receiving means disposed on an area of said sample card; and
   (b) humidity-indicating means mounted on said card in spaced relation apart from the area of said medical sample receiving means.

2. The card of claim 1, which includes:
   (a) a plurality of printed medical sample receiving areas.

3. The card of claim 1, which includes:
   (a) said humidity indicating means comprising a patch adhesively mounted on said card.

4. The card for receiving medical specimens of claim 3 wherein said humidity indicating means includes color-changing means for changing colors responsive to humidity levels on said card, said color-changing means for indicating moisture content on and in said sample cared being reversibly and alterably responsive to changing moisture contents of air at the humidity indicating patch means on said card at a second area.

5. The card of claim 4 wherein said color-changing means comprises a patch of blotting paper impregnated with cobalt chloride.

6. The card of claim 1, which comprises cotton fiber blotting material.

7. A medical sample handling system for collecting, transporting and monitoring a medical sample, which includes:
   (a) a medical sample card having front and back faces, a sample area on said front face for receiving a medical specimen disposed at a first location thereon, and a humidity indicator area on said front face disposed at a second location thereon for indicating the moisture content on and in the medical sample card;
   (b) a humidity-indicating patch including means for changing color in response to changing humidity levels, said patch being mounted on said humidity indicator area of said card;
   (c) an envelope including a pocket for receiving said card; and
   (d) desiccant means receivable in said envelope pocket with said card.

8. (claim 8 rewritten in independent form) A medical sample handling system for collecting, transporting and monitoring a medical sample, which includes:
   (a) a medical sample card having front and back faces, a sample area on said front face for receiving a medical specimen, and a humidity indicator area on said front face for indicating moisture content on and in said sample card;
   (b) a humidity-indicating patch including means for changing color in response to changing humidity levels, said patch being mounted on said humidity indicator area of said card;
   (c) an envelope including a pocket for receiving said card;
   (d) desiccant means receivable in said envelope pocket with said card;
   (e) said sample card being a blood sample card; and
   (f) urine specimen collection means also insertable into said envelope.

9. (claim 9 rewritten in independent form) A medical sample handling system for collecting, transporting and monitoring a medical sample, which includes:
   (a) a medical sample card having front and back faces, a sample area on said front face for receiving a medical specimen, and a humidity indicator area disposed at a second area on said front face for indicating moisture content on and in said sample card;
   (b) a humidity-indicating patch including means for changing color in response to changing humidity levels, said patch being mounted on said humidity indicator area of said card;
   (c) an envelope including a pocket for receiving said card;
   (d) desiccant means receivable in said envelope pocket with said card;
   (e) said envelope pocket comprising a sample card pocket; and
   (f) said envelope also having a urine specimen pocket for receiving said urine specimen collection means.

10. (claim 10 rewritten in independent form) A medical sample handling system for collecting, transporting and monitoring a medical sample, which includes:
    (a) a medical sample card having front and back faces, a sample area on said front face for receiving a medical specimen, and a humidity indicator area disposed at a second area on said front face for indicating moisture content on and in said sample card;
    (b) a humidity-indicating patch including means for changing color in response to changing humidity levels, said patch being mounted on said humidity indicator area of said card;
    (c) an envelope including a pocket for receiving said card;
    (d) desiccant means receivable in said envelope pocket with said card; and
    (e) said sample card pocket being lined with a substantially fluid-impervious layer.

11. (claim 16 rewritten in independent form) A medical sampling method, which includes the steps of:
    (a) providing a blood sample collection card for receiving one or more blood droplets;
    (b) providing a humidity-indicating patch at a specified location on blood sample collection card for indicating moisture content on and in said blood sample collection card;
    (c) mounting said humidity-indicating patch on said blood sample collection card;
    (d) placing a subject's blood droplet on said blood sample collection card at an area different from the specified location of said humidity-indicating patch;

(e) drying said blood droplet while monitoring the color of said humidity-indicating patch;
(f) providing a return mailing envelope with a blood specimen card pocket;
(g) placing said blood sample card in said envelope pocket;
(h) mailing said envelope containing said blood sample card;
(i) providing a urine vial;
(j) obtaining a urine specimen;
(k) sealing said urine specimen in said urine vial;
(l) providing a urine vial pocket in said envelope; and
(m) sealing said urine vial in said urine vial pocket.

12. (claim 17 rewritten in independent form) A medical sampling method, which includes the steps of:
(a) providing a blood sample collection card for receiving one or more blood droplets;
(b) providing a humidity-indicating patch at a specified location on blood sample collection card for indicating moisture content on and in said blood sample collection card;
(c) mounting said humidity-indicating patch on said blood sample collection card;
(d) placing a subject's blood droplet on said blood sample collection card at an area different from the specified location of said humidity-indicating patch;
(e) drying said blood droplet while monitoring the color of said humidity-indicating patch;
(f) providing a fold line extending across said blood sample collection card;
(g) folding said blood sample collection card to a drying configuration; and
(h) drying said blood sample collection card.

13. (claim 18 rewritten in independent form) A medical sampling method, which includes the steps of:
(a) providing a blood sample collection card for receiving one or more blood droplets;
(b) providing a humidity-indicating patch at a specified location on blood sample collection card for indicating moisture content on and in said blood sample collection card;
(c) mounting said humidity-indicating patch on said blood sample collection card;
(d) placing a subject's blood droplet on said blood sample collection card at an area different from the specified location of said humidity-indicating patch;
(e) drying said blood droplet while monitoring the color of said humidity-indicating patch;
(f) providing a test and subject identification form;
(g) preprinting said identification form with barcode indicia;
(h) providing a blood sample collection card label with barcode indicia matching said preprinted barcode indicia printed thereon; and
(i) applying said blood sample collection card label to said blood sample collection card.

14. A medical sample handling system for collecting, transporting and monitoring blood and urine specimens from a subject, which comprises:
(a) a blood specimen collection subsystem including:
 (1) a blood sample card comprising blotter paper and having front and back faces, upper and lower portions, upper and lower edges adjacent to the upper and lower portions respectively, and opposite side edges;
 (2) a card fold line extending across said card substantially midway between said side edges, said card fold line extending between said card upper and lower edges;
 (3) a plurality of blood-droplet receiving circles printed on said card front face upper portion;
 (4) a barcode label area on said card front face lower portion;
 (5) a humidity-indicating patch including means for changing color in response to changing humidity levels, said patch being mounted on said card front face lower portion in fluidic communication with said card;
 (6) said card having a flat, mailing configuration and a drying configuration folded along said fold line and resting on card side edges;
 (7) a lancet; and
 (8) bandage means;
(b) a urine specimen collection subsystem, which includes a urine collection vial with a removable, substantially fluid-tight lid; and
(c) a labeling/mailing subsystem, which includes:
 (1) an envelope having front and back panels, top and bottom edges, first and second side edges and a closure flap, said envelope front and back panels being connected along said upper and lower edges, along one of said side edges and along a medial strip extending in generally parallel, spaced relation between said top and bottom edges;
 (2) said envelope having upper and lower pockets separated by said medial strip;
 (3) an adhesive strip on said closure flap;
 (4) a substantially fluid-impervious liner lining said upper and lower pockets;
 (5) a test and subject information form including a preprinted barcode indicia, a blood specimen card label with barcode indicia matching the barcode indicia preprinted on said form, a urine vial label mounted on said forming and including barcode indicia matching the barcode indicia preprinted on said form;
 (6) a tamper-evident tape strip for placement over said urine vial cover sealing same on said urine vial;
 (7) a desiccant packet receivable in said upper envelope pocket with said blood specimen card;
 (8) a fluid-absorbent pouch adapted for receiving said urine collection vial and receivable in said envelope lower pocket; and
 (9) preprinted return address means on said envelope front panel.

15. A medical sampling method, which includes the steps of:
(a) providing a blood sample collection card for receiving one or more blood droplets;
(b) providing a humidity-indicating patch for indicating the moisture content on and in said collection card;
(c) mounting said humidity-indicating patch at a specified location on said blood sample collection card;
(d) placing a subject's blood droplet on said blood sample collection card at an area different from the specified location of said humidity-indicating patch; and
(e) drying said blood droplet while monitoring the color of said humidity-indicating patch.

16. The method of claim 15, which includes the additional steps of:
 (a) providing a return mailing envelope with a blood specimen card pocket;
 (b) placing said blood sample card in said envelope pocket; and
 (c) mailing said envelope containing said blood sample card.

17. The method of claim 16, which includes the additional steps of:
 (a) providing a desiccant packet; and
 (b) placing said desiccant packet in said envelope pocket.

18. The method of claim 16, which includes the additional steps of:
 (a) providing a urine vial;
 (b) obtaining a urine specimen;
 (c) sealing said urine specimen in said urine vial;
 (d) providing a urine vial pocket in said envelope; and
 (e) sealing said urine vial in said urine vial pocket.

19. The method of claim 15, which includes the additional steps of:
 (a) providing a fold line extending across said blood sample collection card;
 (b) folding said blood sample collection card to a drying configuration; and
 (c) drying said blood sample collection card.

20. The method of claim 15, which includes the additional steps of:
 (a) providing a test and subject identification form;
 (b) preprinting said identification form with barcode indicia;
 (c) providing a blood sample collection card label with barcode indicia matching said preprinted barcode indicia printed thereon; and
 (d) applying said blood sample collection card label to said blood sample collection card.

21. The method of claim 15, which includes the additional steps of:
 (a) providing a lancet; and
 (b) piercing a subject's finger with said lancet to obtain blood droplets therefrom.

22. The method of claim 15, which includes the additional step of:
 (a) placing multiple blood droplets on said blood sample collection card.

* * * * *